(12) United States Patent
Skarda

(10) Patent No.: US 7,331,948 B2
(45) Date of Patent: Feb. 19, 2008

(54) CATHETER AND CATHETER FABRICATION METHOD

(75) Inventor: James R. Skarda, Lake Elmo, MN (US)

(73) Assignee: Medtronic, Inc., Minneapolis, MN (US)

( * ) Notice: Subject to any disclaimer, the term of this patent is extended or adjusted under 35 U.S.C. 154(b) by 79 days.

(21) Appl. No.: 10/871,588

(22) Filed: Jun. 18, 2004

(65) Prior Publication Data

US 2005/0283136 A1  Dec. 22, 2005

(51) Int. Cl.
 *A61M 25/00* (2006.01)
(52) U.S. Cl. .................. 604/527; 604/526; 604/525
(58) Field of Classification Search ......... 604/523–527
 See application file for complete search history.

(56) References Cited

U.S. PATENT DOCUMENTS

| 4,283,447 A | 8/1981 | Flynn ..................... 428/36 |
| 4,321,226 A | 3/1982 | Markling ................. 264/139 |
| 4,531,943 A | 7/1985 | Van Tassel et al. ....... 604/280 |
| 4,551,292 A | 11/1985 | Fletcher et al. .......... 264/139 |
| 4,817,613 A | 4/1989 | Jaraczewski et al. ...... 128/658 |
| 5,078,702 A | 1/1992 | Pomeranz ................ 604/280 |
| 5,221,270 A * | 6/1993 | Parker .................... 604/527 |
| 5,234,416 A | 8/1993 | Macaulay et al. ......... 604/282 |
| 5,509,910 A | 4/1996 | Lunn ..................... 604/282 |
| 5,545,149 A * | 8/1996 | Brin et al. ............... 604/265 |
| 5,676,659 A * | 10/1997 | McGurk .................. 604/527 |
| 5,738,742 A * | 4/1998 | Stevens .................. 156/149 |
| 5,769,796 A * | 6/1998 | Palermo et al. .......... 600/585 |
| 5,964,971 A * | 10/1999 | Lunn ..................... 156/86 |
| 5,972,143 A * | 10/1999 | Stevens .................. 156/149 |
| 6,042,578 A * | 3/2000 | Dinh et al. .............. 604/527 |
| 6,106,510 A | 8/2000 | Lunn et al. .............. 604/525 |
| 6,375,774 B1 | 4/2002 | Lunn et al. .............. 156/158 |
| 6,591,472 B1 * | 7/2003 | Noone et al. ............. 29/417 |

* cited by examiner

*Primary Examiner*—Nicholas D. Lucchesi
*Assistant Examiner*—Laura Bouchelle
(74) *Attorney, Agent, or Firm*—Carol F. Barry; Steve Bauer

(57) ABSTRACT

A catheter is fabricated by joining a first catheter body segment, the first segment including a braided or coiled filament reinforcing layer contained within an outer layer, to a second catheter body segment by thermal fusion in a zone including an interface between the first segment and the second segment and at a temperature causing ends of the filament reinforcing layer in the zone to extend outward within the outer layer. Following thermal fusion, the extending ends of the filament reinforcing layer are removed.

29 Claims, 4 Drawing Sheets

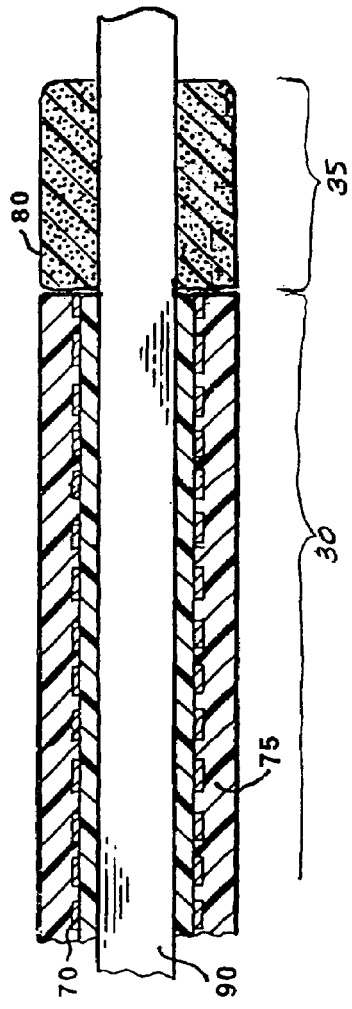
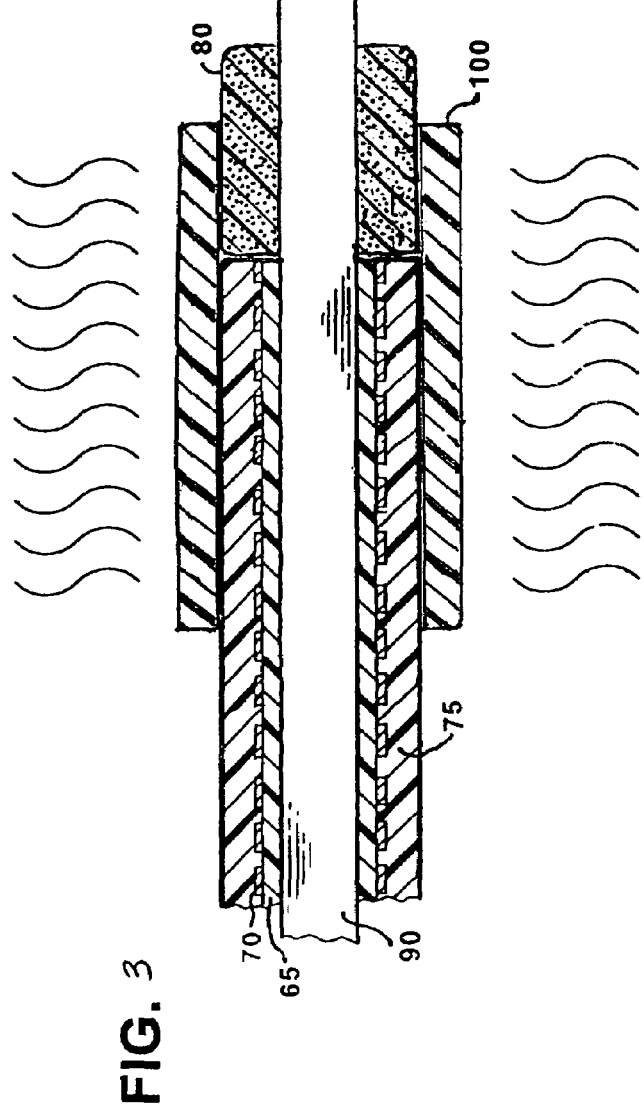
FIG. 2
FIG. 3

CATHETER AND CATHETER FABRICATION METHOD

TECHNICAL FIELD

The present invention pertains to the manufacture of catheter bodies formed of two or more catheter body segments, and particularly to means for forming junctions between catheter body segments.

BACKGROUND

Medical catheters are adapted for insertion into a body cavity, duct, tract, organ or blood vessel in order to facilitate any of a wide variety of diagnostic or therapeutic functions. Such catheters generally include an elongated, flexible catheter tube or body whose side wall encloses at least one catheter lumen extending from a proximal catheter body end, which is coupled to a catheter hub, to a distal catheter body end. The catheter body may be relatively straight or inherently curved or curved by insertion of a curved stiffening wire or guide wire or curved by built-in control wire-deflection. The catheter sidewall is typically fabricated and dimensioned to minimize a catheter body outer diameter and sidewall thickness and to maximize the catheter lumen diameter while retaining sufficient sidewall flexibility and strength characteristics to enable the catheter to be used for the intended medical purpose. Examples of medical catheters include but are not limited to electrophysiology catheters, guiding catheters, drainage catheters, perfusion catheters and drug infusion catheters.

Desirable qualities of catheters include a stiffness facilitating torque transfer and pushability balanced with a flexibility facilitating tracking through tortuous anatomy, lumen lubricity to facilitate passage of other catheters or devices or substances therethrough, and a sidewall strength that prevents kinking. Additionally, it is desirable to provide a smooth and relatively soft catheter distal tip, to prevent damage to surrounding tissue as catheter is advanced, and a radiopaque marker near the distal tip to enhance catheter visibility under fluoroscopy. To achieve the aforementioned qualities it may be necessary to form a catheter body from a plurality of segments.

A typical technique employed to join catheter body segments involves assembling a mandrel through the lumens of catheter body segments and then fusing the segments together by means of heat applied while the segments are held within a tube, for example a PTFE tube. Frequently, the joint that is achieved is enlarged or is flawed in other respects. If one of the catheter segments includes reinforcement in the form of braided or coiled wire filaments or strands within a sidewall, the strands, in proximity to the fused joint, may unravel or shift such that they protrude out through the outer surface of the fused joint. This can occur due to a high tensile strength of the wire filaments and the winding tension that is applied during formation of a tight wire braid or coil. There remains a need for a fabrication technique that simplifies fabrication steps and reduces scrap and other costs while retaining desirable characteristics of the catheter body.

BRIEF DESCRIPTION OF THE DRAWINGS

The following drawings are illustrative of particular embodiments of the invention and therefore do not limit its scope, but are presented to assist in providing a proper understanding of the invention. The drawings are not to scale (unless so stated) and are intended for use in conjunction with the explanations in the following detailed description. The present invention will hereinafter be described in conjunction with the appended drawings, wherein like numerals denote like elements and:

FIG. 2 is a longitudinal section view of catheter segments according to an initial assembly step of a method of the present invention;

FIG. 3 is a longitudinal section view of the catheter segments according to another assembly step of the method;

DETAILED DESCRIPTION OF THE DRAWINGS

The following detailed description is exemplary in nature and is not intended to limit the scope, applicability, or configuration of the invention in any way. Rather, the following description provides a practical illustration for implementing exemplary embodiments of the invention.

Figure 1:
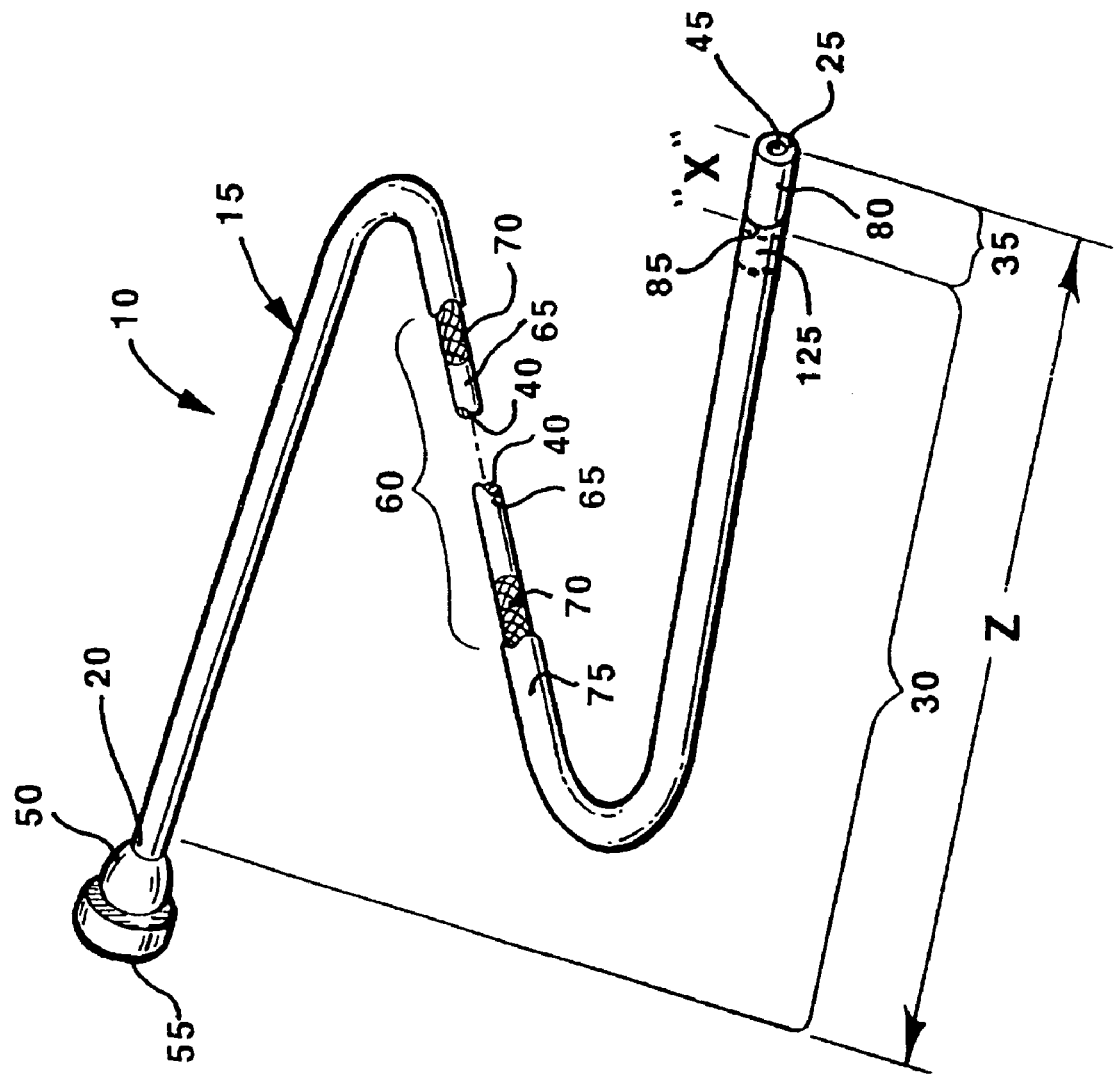
FIG. 1 is a perspective view of an exemplary medical catheter according to one embodiment of the present invention.

FIG. 1 is a perspective view of an exemplary medical catheter according to one embodiment of the present invention; FIG. 1 is intended to be representative of any single lumen or multi-lumen medical catheter having at least two catheter body segments that are joined together. FIG. 1 illustrates a catheter 10 including a catheter body 15 and a hub 50 terminating a proximal end 20 thereof; hub 50 can include any standard medical interconnection, for example a luer fitting, that provides for the introduction of an agent or device through catheter lumen 40; hub 50 may further function as a handle and or a connector being configured to manipulate catheter body and or power electrodes (not shown) of catheter 10.

FIG. 1 further illustrates catheter body 15 including a lumen 40, extending between proximal catheter body end 20 and a distal catheter body end 25, a proximal catheter body segment 30 and at least one distal catheter body segment 35 having a length "X" and being joined to segment 30 at junction 85. According to the illustrated embodiment, lumen 40 extends over a length "Z" of catheter body 15, from a lumen distal opening 45 to a lumen proximal opening 55, and is formed by a tubular inner jacket or liner 65, which will be described below. Selecting the relative lengths and mechanical characteristics of each of these catheter body segments controls the pushability, torqueability, rupture and kink resistance, and flexibility of catheter body 15. For a wide range of catheters, "X" can be selected in a range between approximately 0.2 cm and approximately 30 cm, and "Z" can be selected in a range between approximately 30 cm and approximately 200 cm.

According to embodiments of the present invention, proximal catheter body segment 30 includes a reinforcing layer 70 disposed between inner liner 65 and an outer sheath 75, as shown in an exposed section 60 in FIG. 1; segment 30 may have been cut from a greater length of stock tubing that had been fabricated in bulk according to methods known to those skilled in the art. Examples of materials that may be used to form liner 65 include fluorocarbon polymers, polyamides (e.g., Nylon), polyether block amides (PEBA), polyolefins, and polyimides; according to an exemplary embodiment, liner 65 is extruded of PEBAX® polyether block-polyamide having a hardness in the range of approximately 55D to approximately 70D. Layer 70 is formed of wire filaments braided together or coiled over and against an outer surface of inner liner 65 in a continuous or discontinuous braiding or winding operation. According to an exemplary embodiment, rectangular or flat wire filaments of stainless steel are used to form the braid or coil; for example, a number of flat 304V stainless steel ribbon wires having a tensile strength between approximately 100 kpsi and approximately 400 kpsi are wound under tension into a braid configuration, of typically 20-50 picks per inch, over the outer surface of liner 65. According to some embodiments of the present invention, outer sheath 75 is formed over reinforcing layer 70 by a continuous extrusion process so that the outer sheath material penetrates interstices between the wire filaments of layer 70 and is of uniform thickness, within acceptable tolerances. Examples of materials appropriate for outer sheath 75 include polyamide polyether block amides, (PEBAX® or VESTAMID®), polyurethane, polyethylene, silicone rubber, polyimides, polyamides, fluorinated hydrocarbon polymers and the like having a hardness in the range from approximately 90A to approximately 75D; outer sheath 75 may be tinted, for example with a blue tint, to provide an attractive and more visible appearance.

FIG. 1 further illustrates distal segment 35 formed by a tube 80 having an outer diameter approximately equal to or less than an outer diameter of outer sheath 75 and a filler segment 125 positioned just proximal to junction 85; there is no ridge of increased diameter or groove of decreased diameter at or in proximity to junction 85. According to an some embodiments, tube 80 forms a tip or distal catheter body segment 35 being softer or more flexible than proximal segment 30; tube 80 may have been cut to length "X" from a longer length of stock tubing that has been extruded, in a continuous extrusion process and examples of materials from which tube 80 is formed include, but are not limited to polyamide polyether block amides (PEBAX® or VESTAMID®), polyurethane, polyethylene, silicone rubber, polyimides, polyamides, fluorinated hydrocarbon polymers. Furthermore, radiopaque materials, for example barium sulfate or platinum particles, may be incorporated into the material selected for fabrication of tube 80. According to embodiments of the present invention, filler segment 125 has been formed in proximity to junction 85 as a final step of an operation joining proximal and distal catheter body segments 30 and 35.

Figure 4:
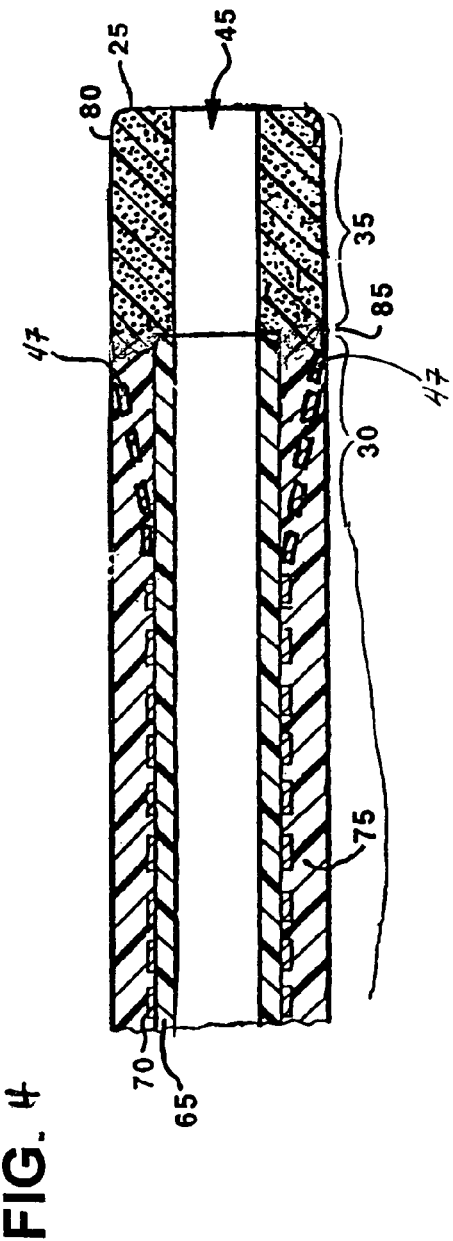
FIG. 4 is a longitudinal section view of the catheter segments joined by the step illustrated in FIG. 3.

FIGS. 2-7 are longitudinal section views of portions of catheter 10 at various points in time during a fabrication method, which is exemplary of embodiments of the present invention. FIGS. 2-7 illustrate the fabrication method whereby junction 85 and filler segment 125 are formed. FIG. 2 shows distal segment 35 butted up to proximal segment 30, both segments being supported by a mandrel 90, according to an initial step of an exemplary method; according to an alternate step one of segments 30 and 35 may overlap the other segment. Mandrel 90 may include a fluoropolymer coating. FIG. 3 shows a tube 100, for example a PTFE tube, fitted over segments 30 and 35 and spanning the abutting ends of the segments to assure intimate contact therebetween during a thermal fusion process illustrated by wavy lines; a temperature applied during the thermal fusion process should cause both a material forming segment 30 and a material forming segment 35 to melt thereby forming a bond between the materials via intermixing of the materials. Additional longitudinal forces may be applied to segments 30 and 35 to assure their intimate contact during the fusion process. According to an exemplary embodiment of the present invention, outer layer 75 of proximal segment 30 is formed of 72D durometer PEBAX® and tube 80 of distal segment 35 is formed of a softer PEBAX®, for example between 55D and 65D durometer; in this case the temperature applied for fusing segments 30 and 35 must be sufficient to melt the harder 72D PEBAX®, for example between approximately 300° and 400° F. Following the fusion step illustrated in FIG. 3, materials of segments 30 and 35 are allowed to cool and solidify and then tube 100 is removed; the resulting junction 85 is illustrated in FIG. 4.

Figure 5:
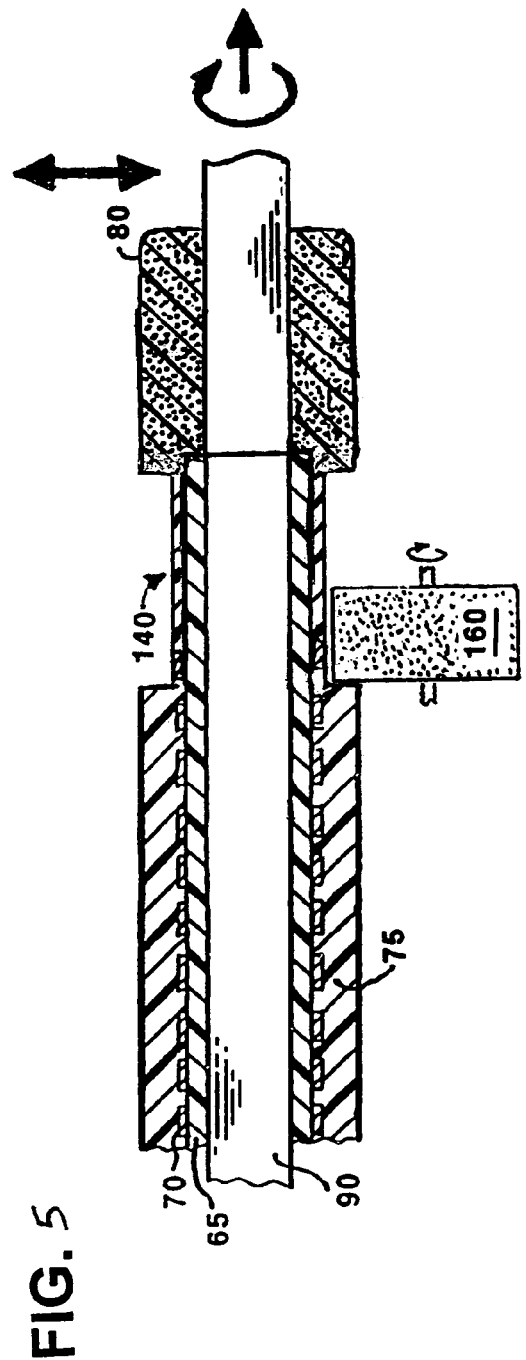
FIG. 5 is a longitudinal section view of the catheter segments according to another assembly step of a method of the present invention.

FIG. 4 further illustrates ends 47 of filament reinforcing layer 70, in proximity to junction 85, which have extended out within outer sheath 75 during the fusion step; the heat and or forces applied to segment 30 during fusion has caused filament reinforcing layer to expand and shift. In some cases ends 47 may protrude from an outer surface of outer sheath 75 and or junction 85 while in other cases ends 47 may remain just below the outer surface; since neither case is desirable, ends 47 are removed in a subsequent step according to methods of the present invention. FIG. 5 illustrates an example of such a fabrication step wherein outwardly extending ends 47, depicted in FIG. 4, have been removed by means of a grinding process, which forms channel 140. According to the illustrated step, mandrel 90 supports the assembly of segments 30 and 35 and a grinding wheel 160 is mounted to rotate on an axis extending in parallel with the axis of the mandrel 90. The grinding wheel 160 may be a conventional grit wheel or a diamond or carbide blade. A fixture (not shown) holds mandrel 90 such that a zone of the assembly encompassing ends 47 is positioned in operative relation to the grinding wheel 160; with reference to the arrows shown in FIG. 5, the fixture further moves the assembly laterally toward and away from grinding wheel 160, rotates the assembly about the axis of mandrel 90 and moves the assembly axially.

According to the method step illustrated in FIG. 5, the assembly of segments 30 and 35 are moved laterally toward grinding wheel 160, rotated about the axis of mandrel 90 and moved axially as grinding wheel 160 is rotated so that outer sheath 75 and ends 47 are ground away and channel 140 is formed extending around a circumference of segment 30; a micrometer may be employed in the fixture to set stops governing a depth of channel 140. According to an alternate embodiment, channel 140 may further extend lengthwise into segment 35; furthermore, the grinding wheel 160 may be of a width corresponding to a predetermined length of channel 140 so that axial movement is unnecessary. In a fully automated assembly process, the length and depth of channel 140, along with positions of proximal and distal ends of channel 140, would be dictated by preprogrammed settings for a computer-controlled fixture.

Figure 6:
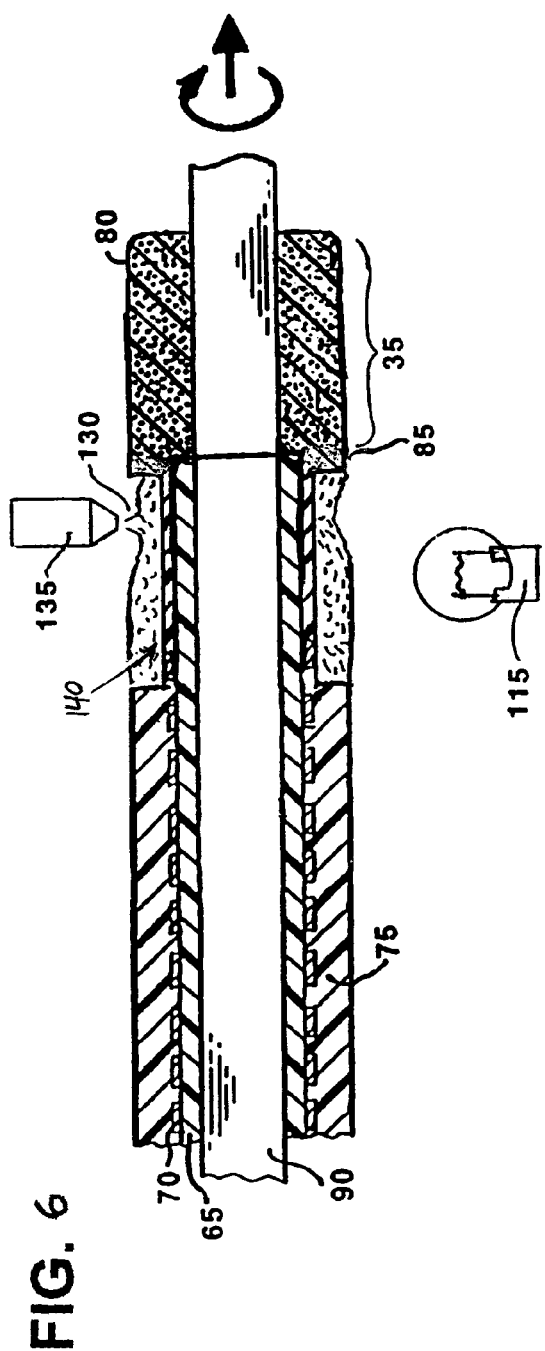
FIG. 6 is a longitudinal section view of the catheter segments according to yet another step of a method of the present invention.
Figure 7:
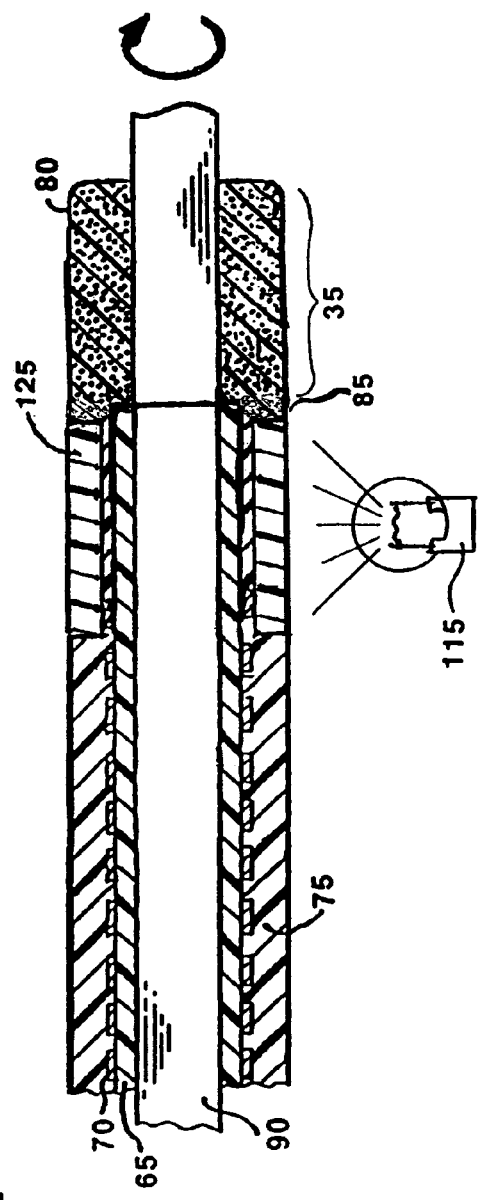
FIG. 7 is a longitudinal section view of the catheter segments according to a final assembly step of a method of the present invention.

Whether outwardly extending ends 47 are removed according to the process described in conjunction with FIG. 5 or according to an alternate process, preferred embodiments of the present invention further include a method filling voids left by the removed ends 47; FIGS. 6 and 7 illustrate an example of such a method. FIG. 6 illustrates a step of the exemplary method wherein channel 140 is filled with a material 130, preferably a polymer compatible with the polymers of segments 30 and 35, adheres well therewith and self-levels in channel 140. According to one embodiment filler material 130 is a liquid epoxy while, according to a preferred embodiment, filler material 130 is a UV light curable polymer, e.g., a biocompatible UV light curable medical adhesive, and curing is effected by exposing filler 130 to UV light as shown schematically in FIG. 7. An example of an appropriate UV light curable polymer is type 1191-M polyurethane oligomer mixture available from Dymax Corp., Torrington, Conn., which includes about 40%-50% polyurethane oligomer suspended in solvents that are driven off during curing; another example is a Loctite® Type 3341 light cured medical adhesive available from Henkel Loctite Corp., Rocky Hill, Conn., which includes about 35%-45% aliphatic polyurethane acrylic oligomers suspended in solvents that are driven off during curing. Both of these light curable polymers cure under UV light in about 30 seconds to form filler segment 125 illustrated in FIG. 1. Moreover, a Shore durometer or hardness of the resulting filler segment 125 may be selected to be intermediate the Shore durometer of the outer sheath 75 and the distal tube 80.

An adhesive applying and curing fixture may be employed to accomplish the formation of filler segment 125; the fixture would support a mandrel, e.g. mandrel 90 on which the assembly of segments 30 and 35 are mounted, and cause rotation and axial movement of the assembly as indicated by the arrows of FIG. 6 while filler 130 is dispensed from a source 135. The fixture may further include a microscope for an operator to view channel 140 as it is filled. According to preferred embodiments, filler material 130 has a viscosity and surface tension characteristics ensuring that filler 130 remains within the channel 140 and self-levels during such movement of the assembly of segments 30 and 35. FIGS. 6 and 7 further illustrates the fixture including a UV light source 115 that is turned on, as shown schematically in FIG. 7, following the filling step of FIG. 6, to cure filler material 130; the assembly of the of segments 30 and 35 is rotated, as shown by the arrow of FIG. 7, until curing is complete. Preferably, filler 130 cures without substantial shrinkage or expansion resulting in catheter body 15 including filler segment 125 as described in conjunction with FIG. 1.

In the foregoing detailed description, the invention has been described with reference to specific embodiments. However, it may be appreciated that various modifications and changes can be made without departing from the scope of the invention as set forth in the appended claims.

What is claimed is:

1. A catheter fabrication method, comprising the steps of:
   joining a first catheter body segment, the first segment including a braided or coiled filament reinforcing layer contained within an outer layer, to a second catheter body segment by thermal fusion in a zone including an interface between the first segment and the second segment and at a temperature causing ends of the filament reinforcing layer in the zone to extend outward within the outer layer; and
   removing the extending ends of the filament reinforcing layer.

2. The method of claim 1, wherein the step of removing the extending ends creates a channel in an outer surface of the outer layer.

3. The method of claim 1, wherein the step of removing the extending ends creates a channel in an outer surface of the outer layer and in an outer surface of the second catheter segment.

4. The method of claim 1, wherein the step of removing the extending ends comprises grinding away the extending ends.

5. The method of claim 1, further comprising the step of filling a void left by the removed extending ends with a material.

6. The method of claim 2, further comprising the step of filling the channel with a material to create a smooth transition between the outer surface of the outer layer and an outer surface of the second catheter segment.

7. The method of claim 6, wherein the material is an epoxy.

8. The method of claim 6, wherein the material is a polymer.

9. The method of claim 6, further comprising the step of curing the material filling the channel.

10. The method of claim 9, wherein the material is a UV light curable polymer.

11. The method of claim 6, wherein the material has a hardness greater than that of the second segment.

12. The method of claim 6, wherein the material has a hardness less than that of the outer layer of the first segment.

13. The method of claim 1, wherein:
   the outer layer of the first segment is formed of a polyether block amide having a hardness between approximately 70 and approximately 75 on a Shore D scale and the second segment is formed of a polyether block amide having a hardness between approximately 50 and approximately 70 on a Shore D scale; and
   the thermal fusion temperature is between approximately 300° F. and approximately 400° F.

14. A catheter fabrication method, comprising the steps of:
   joining a first catheter body segment, the first segment including a braided or coiled filament reinforcing layer contained within an outer layer, to a second catheter body segment by thermal fusion in a zone including an interface between the first segment and the second segment and at a temperature causing ends of the filament reinforcing layer in the zone to extend outward within the outer layer;
   removing the extending ends of the filament reinforcing layer and thereby creating a channel in an outer surface of the outer layer; and
   filling the channel with a material to create a smooth transition between an outer surface of the outer layer and an outer surface of the second catheter segment.

15. The method of claim 14, wherein the step of removing the extending ends comprises grinding away the extending ends.

16. The method of claim 14, wherein the material is an epoxy.

17. The method of claim 14, wherein the material is a polymer.

18. The method of claim 14, further comprising the step of curing the material filling the channel.

19. The method of claim 18, wherein the material is a UV light curable polymer.

20. The method of claim 14, wherein the material has a hardness greater than that of the second segment.

21. The method of claim 14, wherein the material has a hardness less than that of the outer layer of the first segment.

22. The method of claim 14, wherein:
   the outer layer of the first segment is formed of a polyether block amide having a hardness between approximately 70 and approximately 75 on a Shore D scale and the second segment is formed of a polyether block amide having a hardness between approximately 50 and approximately 70 on a Shore D scale; and the thermal fusion temperature is between approximately 300° F. and approximately 400° F.

23. A catheter, comprising:

a first catheter body segment including a braided or coiled filament reinforcing layer contained within an outer layer;

a second catheter body segment joined to the first catheter body segment by thermal fusion; and a zone, in close proximity to the junction of the first segment and the second segment, including a channel, the channel having been formed by removing ends of the filament reinforcing layer and being filled with a material to create a smooth transition between an outer surface of the outer layer and an outer surface of the second catheter segment;

wherein the ends of the filament reinforcing layer were caused to extend outward within the outer layer by the thermal fusion.

24. The catheter of claim 23, wherein the material is a UV light curable polymer.

25. The catheter of claim 23, wherein the material has a hardness greater than that of the second segment.

26. The catheter of claim 23, wherein the material has a hardness less than that of the outer layer of the first segment.

27. The catheter of claim 23, wherein the outer layer of the first segment is formed of a polyether block amide having a hardness between approximately 70 and approximately 75 on a Shore D scale and the second segment is formed of a polyether block amide having a hardness between approximately 50 and approximately 70 on a Shore D scale.

28. A catheter fabrication method, comprising the steps of:

joining a first catheter body segment, the first segment including a braided or coiled filament reinforcing layer contained within an outer layer, to a second catheter body segment by thermal fusion in a zone including a butt joint between the first segment and the second segment and at a temperature causing ends of the filament reinforcing layer in the zone to extend outward within the outer layer;

removing the extending ends of the filament reinforcing layer and thereby creating a channel spanning a portion of an outer surface of the first segment and a portion of an outer surface of the second segment; and filling the channel with a material to create a smooth transition between the outer surface of the first segment and the outer surface of the second segment;

wherein the joining comprises placing a heat-resistant tube spanning the butt joint prior to the thermal fusion process to promote intimate contact of the first and second segments; and removing the tube subsequent to the thermal fusion process.

29. A catheter fabrication method, comprising the steps of:

joining a first catheter body segment, the first segment including a braided filament reinforcing layer contained within an outer layer, to a second catheter body segment by thermal fusion in a zone including an interface between the first segment and the second segment and at a temperature causing ends of the filament reinforcing layer in the zone to extend outward within the outer layer; and removing a portion of the braided filament reinforcing layer.

* * * * *